United States Patent [19]

Streber

[11] Patent Number: 5,102,912

[45] Date of Patent: Apr. 7, 1992

[54] HYDROXYOCTADECADIENIC ACID FOR THE TREATMENT OF ESTROGEN-DEPENDENT DISEASE

[75] Inventor: August S. Streber, Aichen, Fed. Rep. of Germany

[73] Assignee: Kanoldt Arzneimittel GmbH, Fed. Rep. of Germany

[21] Appl. No.: 687,308

[22] Filed: Apr. 18, 1991

[30] Foreign Application Priority Data

Oct. 24, 1990 [EP] European Pat. Off. ........ 90120434.7

[51] Int. Cl.$^5$ ...................... A01N 37/00; A61K 31/20
[52] U.S. Cl. .................... 514/529; 514/549; 514/558; 514/560; 514/693; 514/705; 514/874
[58] Field of Search ............... 514/529, 459, 558, 560, 514/693, 705, 874

[56] References Cited

U.S. PATENT DOCUMENTS 4,724,234  2/1988  Cone, Jr. .............................. 514/558
4,950,688  8/1990  Bowser et al. ...................... 514/873

*Primary Examiner*—Nathan M. Nutter
*Attorney, Agent, or Firm*—Pravel, Gambrell, Hewitt, Kimball and Krieger

[57] ABSTRACT

This invention describes the use of a hydroxyoctadecadienic acid, its acid oxidized to keto form or the ester derivatives of the acids, where the ester derivatives are low esters with 1 to 4 carbon atoms for the preparation of a pharmaceutical for treatment of breast carcinomas or benign prostatic hyperplasia. In particular, those compounds are suitable in which the double bonds and the hydroxy group or the oxo group are present on the carbon atoms at positions 9 to 13.

19 Claims, No Drawings

HYDROXYOCTADECADIENIC ACID FOR THE TREATMENT OF ESTROGEN-DEPENDENT DISEASE

FIELD OF THE INVENTION

This invention concerns the use of hydroxyoctadecadienic acid, its acid oxidized to keto form or its derivatives for the treatment of estrogen-dependent disease, especially for the treatment of breast carcinoma or of benign prostatic hyperplasia as well as pharmaceutical preparations containing these substances.

BACKGROUND OF THE INVENTION

Malignant or benign tumors whose cell growth is controlled by sexual hormones include prostatic tumors, benign prostatic hyperplasia and breast carcinomas. Benign prostatic hyperplasia can be caused by a reduction of androgens, which is associated with a relative increase in the share of estrogens in the hormone balance.

However, not only the reduction of androgens but also increased estrogen production caused by increased aromatase activity in males is regarded today as a cause of benign prostatic hyperplasia. The rich connective tissue of the prostate is particularly responsive to estrogens with activated growth. Benign prostatic hyperplasia is caused and continues to grow due to faulty control of hormones. Thus an "organ" grows but not a type of tissue, i.e. benign prostatic hyperplasia consists of connective tissue and glandular epithelium, which form irregular nodes, e.g. glands without the associated excretory duct. Now both types of cells require two different and opposite hormones for their growth impulse. The glandular cells respond to androgens (e.g. testosterone), the connective tissue, on the other hand, reacts to estrogens (e.g. estradiol).

Symptoms which arise in prostatic hyperplasia include an increased desire to urinate, problems when passing water, later residual urine, and lastly, an acute urine blockage, because due to the expanding tissue in the surroundings of the urethra, the passing of water is choked and is displaced. It is therefore necessary for therapy, which is to improve the miction of a patient made more difficult by the tumor, to increase the miction volume and thereby to reduce or overcome the residual amount of urine.

The enzyme aromatase plays an important part in the normal biosynthesis of the female sexual hormone, estradiol. This enzyme catalyzes the conversion of androgens into estrogens, e.g. of the initially arising testosterone into estradiol (aromatization). Thus the daily use of testosterone in the case of females because of this physiological synthesis route amounts to about 0.1 mg.

Aromatase is an enzyme system of cytochrome P-450 with a NADPH-dependent cytochrome reductase. Non-steroidal aromatase inhibitors (e.g. imidazoles, aminoglutethimide) take effect primarily as inhibitors by reversible complex formation with a haemo group of the enzyme, whereas steroidal inhibitors bind firmly and stop the enzyme system for long periods.

In females, as well as, on a lower level, in males, the conversion of androgens into estrogens is inhibited by aromatase inhibitors, so that a reduction of the estrogen level results. Such aromatase inhibitors were previously used for the treatment of breast carcinoma and in the first tests for cases of benign prostatic hyperplasia. Because they are still disproportionately expensive and in contrast to the carcinoma, the benign prostatic hyperplasia has a comparatively low degree of suffering, they are not represented on the market for prostatic preparations.

Because the agents and substances previously used in the treatment of prostatic carcinoma are produced in very expensive synthetic processes, there is a need for effective substances for aromatase inhibition, which can be used successfully for the treatment of breast carcinoma and prostatic hyperplasia, but which either occur naturally or are synthesized relatively economically.

Oxooctadecadienic acids are known compounds and are used in medicine for specific purposes. For example, in Japanese laid open application JP 62-164620-Al, the use of the unsaturated fatty acid in hydroxy form, is named as an anti-hypertensive agent, and an anti-arteriosclerosis effect is ascribed very generally to unsaturated fatty acids. In a further publication, EP-A-O-097 059, topical compositions which contain these hydroxy acids are suggested for skin treatment.

From Chemical Abstracts, Vol. 93 (1980), NO. 202348a, it is known that 9-hydroxy-10, 12-octadecadienic acid is an (in-vitro) metabolic product of linoleum acid in $VX_2$-tumor tissue culture. In this connection the metabolism of this fatty acid is discussed with respect to its part in the calcium level of bones.

From Chemical Abstracts, Vol. 85 (1976), No. 173098w, 8-hydroxy-10(trans)-12(Cis)-octadecadienic acid and 13-hydroxy-9(cis)-11(trans)-octadecadienic acid as well as the acids oxidized to keto form of these two named acids as well as partial their methylesters are known. These acids can be isolated from the mitochondria of bovine hearts.

From Chemical Abstracts, Vol. 106 (1987), No. 38127k, lastly, 9-hydroxy-10(trans)-12(cis)-octadecadienic acid is known which is used as a protective substance in rice plants. In the two last-named publications, however, no indication is given of the pharmacological properties of the acids described there. In particular, nothing is known about a pharmacological activity of the oxoctadecadienic acids.

SUMMARY OF THE INVENTION

The present invention is based on the object of disclosing hydroxyoctadecadienic acids, which because of their aromatase inhibiting effects can be used successfully for the treatment of tumors and other diseases which are controlled by female sexual hormones.

For the first time a substance is provided by the acids of the invention which has both an anti-androgenous effect as well as an anti-estrogen effect in the form of aromatase inhibition.

DETAILED DESCRIPTION OF THE INVENTION

Hydroxyoctadecadienic acid, its acid oxidized to keto form or its ester derivatives are used for the preparation of a pharmaceutical for the treatment of estrogen-dependent diseases, especially for the treatment of breast carcinoma or benign prostatic hyperplasia.

Preference is given to those hydroxy- and/or oxooctadecadienic acids, in which the two double bonds and the hydroxy group or the oxo group are present on the carbon atoms of positions 9 to 13. According to the invention it is also possible that more than one hydroxy or oxo groups are present in a molecule. Thus, for example, up to three hydroxy or oxo groups may be present per molecule. Of these compounds, the trihydroxyoctadecadienic acid is especially suitable.

It was found in accordance with the invention that the initially named hydroxyoctadecadienic acid or its acid oxidized to keto form, the oxooctadecadienic acid which has preferably in positions 10 or 11 a transconfiguration and in positions 12 or 9 a cis-configuration is particularly suitable for the preparation of pharmaceuticals for the treatment of estrogen-dependent diseases. The following four acids are especially suitable in this invention:

9-hydroxy-10(trans)-12(cis)-octadecadienoic acid,
9-oxo-10(trans)-12(cis)-octadecadienoic acid,
13-hydroxy-9(cis)-11(trans)-octadecadienoic acid and
13-oxo-9(cis)-11(trans)-octadecadienoic acid.

It was found surprisingly that the keto form of the 9-hydroxy acid has a 10-fold better effect by comparison with this hydroxy compound in the treatment of estrogen-dependent diseases.

Instead of the acids, their corresponding ester derivatives can also be used as therapeutic agents, because the enzyme esterase, present in the body, is able to convert the ester into the free acid. In particular, the low alkyl esters having 1 to 4 carbon atoms are suitable as ester derivatives for use in the treatment of estrogen-dependant disease.

Hydroxyoctadecadienic acids occur naturally in vegetable and animal tissues and can be isolated from them. In vegetable extracts of nettle roots, the named acids are present both isolated and as ester components of glycerides, ceramides and phospholipids. But these named hydroxyoctadecadienic acids can also be generated semi-synthetically from oleic acid and from linoleic acid. From technical linoleic acid, which contains up to 30% of oleic acid, these acids can be prepared relatively economically with good yield.

The administration of the respective active ingredient can be performed orally by tablets, capsules or dragees or by injections, particularly intramuscularly, and the solution of the active substance can constitute either an oily or a diluted ethanol solution.

A preferred pharmaceutical preparation in tablet form contains:

9-hydroxy-10(trans)-12(cis)-octadecadienic acid,
9-oxo-10(trans)-12(cis)-octadecadienic acid,
13-hydroxy-9(cis)-11(trans)-octadecadienic acid, or 13-oxo-9(cis)-11(trans)-octadecadienic acid as well as optionally further additives wherein preferably lactose or maltodextrine as well as calcium-carboxymethyl cellulose are added as adjuvants.

The pharmaceutical preparation can be administered in a single dose in an amount of about 50.0 to 200 mg of the active substance per administration form. The daily dose for an adult person is generally within the range of from about 100 to 1000 mg, preferably about 200 to 500 mg, of the active substance.

A preferred pharmaceutical preparation which is administered in the form of soft gelatine capsules contains the following contents:

| | |
|---|---|
| 9-hydroxy-10(trans)-12(cis)-octadecadienic acid | 150 mg |
| soya oil | 150 mg |
| with gastric juices-resistant coating | 300 mg |

For intramuscular injection, instant injections are suitable for 1 cm 3 wherein the mixture is equally 1:1, but for this purpose triglycerides of average size, preferably having 8 to 12 C atoms, are more preferred.

| | |
|---|---|
| 9-hydroxy-10(trans)-12(cis)-octadecadienic acid | 500 mg |
| triglyceride | 500 mg |
| instant injection | 1000 mg |

EXAMPLES

The preparation of 9-hydroxy-10(trans)-12(cis)-octadecadienic acid as well as the preparation of the corresponding 9-oxo-10(trans)-12(cis)-octadecadienic acid oxidized to keto form will be described below. The preparation of the other hydroxy acids or the corresponding oxo acids can be done analogously or by one of the known processes mentioned above.

EXAMPLE 1

Preparation of 9-hydroxy-10(trans)-12(cis)-octadecadienic acid

A mass of 30 g linoleic acid (technical grade, Fluka, Neu-Ulm) is emulsified in 1.8 l phosphate buffer, pH 5.5. (96 parts 1/15 molar $KH_2PO_4$ solution and 4 parts 1/15 molar $Na_2HPO_4$ solution) together with 20 ml TWEEN $20^R$ (emulsifier) by strong shaking. This substrate solution, after repeated shaking, is added to a suspension of 2.5 to 3 kg. of homogenized tomatoes (complete) in approximately 7 l phosphate buffer, Ph 5.5. The pH value of the mixture is adjusted with concentrated $Na_2HPO_4$ solution as precisely as possible to 5.3-5.5 and the mixture is stirred for 5 to 7 hours slowly with access of air. Then it is acidified cautiously with 30% $H_2SO_4$ to pH 2-3 and about 4 to 5 l of ether are added. After about 15 minutes of strong stirring of the total mixture, the gel-type orange ether phase is decanted off and separated by centrifugation from water. Further ether (about 1:1) and about 100 g $Na_2SO_4$ (anhydrous) are added to the gel-type ether phase and shaken. The clear ether solution is decanted off from the flocculated residue, and the latter is again extracted three times with ether. The dried, clear ether phase is concentrated in vacuum at 30° C. The raw hydroxy peroxide and the non-converted initial material remain as red-colored oil (about 30 to 40 g).

The mixture is immediately suspended without purification in 150 ml 0.1 molar borax solution (pH 9) with the addition of 150 ml MeOH and 5 g sodium boro hydride (Fluka), added in portions to the mixture cooled in ice. After the addition is completed, the refrigeration is removed and stirring is performed for two hours at room temperature. After cautions acidification to pH 2-3 with aqueous HCl, the mixture is twice extracted with $CH_2Cl_2$ and the latter phase is washed with NaCl solution. After removal of $CH_2Cl_2$ on a rotation evaporator, the target compound is obtained as a raw product (about 30 g).

The raw product is purified by double column chromatography on respectively about 800 g silica gel with cyclohexane/ethyl acetate/acetic acid (150:100:2 or 250:100:2) (DC control, Rf=0,43 on polygram$^R$ Sil G/UV (Machery & Nagel) with cyclohexane/etOAc/AcOH 100:50:2). About 7 to 8 g of the 9-hydroxy-10(trans)-12(cis)-octadecadienic acid (D-enantiomer) are obtained as a viscous yellow oil (at room temperature) which is only storable to a limited extent even at minus 20° C.

EXAMPLE 2

Preparation of 9-oxo-10(trans)-12(cis)-octadecadienoic acid

A mass of 0.6 g of 9-hydroxyoctadecadienic acid is dissolved with stirring in 60 ml dry methylene chloride and 4 g $MnO_2$ (activated as in Attenboroough, Fluka-90%) are added. The suspension is stirred in the dark for 15 hours at room temperature and is filtered through Celite$^R$. After removal of the solvent, the residue is separated on silica gel plates with cyclohexane/EtOAc/MeOH (70:30:2).

The residue from the elution of the band with Rf=0.35 to 0.40 is respectively recrystallized once from n-hexane and MeOH/$H_2O$ and is dried. About 0.1 g 9-oxo-10(trans)-12(cis)-octadecadienoic acid is obtained which is equally unstable as the product of Example 1.

EXAMPLE 3

Inhibition of Aromatase Activity with 9-hydroxy-10(trans)-12(cis)-octadecadienic acid Inhibitor tests were carried out with a suspension of human placenta microsomes as a source of aromatase enzyme. The substrate used in these competitive inhibition tests was androstenedione. The test conditions are summarized in table 1.

TABLE 1

| Experimental conditions for enzyme inhibition | |
|---|---|
| Volume of test batch: | 500 ul |
| enzyme source: | placenta microsomes 40 ug protein |
| substrate: | androstenedione (10 nM) |
| tracer: | $^3$H-androstenedione |
| Co-substrate: | NADPH-regenerating system (0.5 mM) |
| incubation time: | 10 minutes |
| measured product: | $^3H_2O$ |
| detection: | LSC |

The substrate, $^3$H-androstenedione was incubated in the presence of aromatase enzyme with and without the acid inhibitor. The aromatization of androstenedione to estradiol was measured by the release of $^3H_2O$ in the process of aromatization. Aromatase activity in the presence of 9-hydroxy-10(trans)-12(cis)-octadecadienoic acid was compared with that of a control group without this inhibiting additive. Aromatase activity is shown as percent of reaction in table 2.

TABLE 2

| Aromatase Activity (pMol/10 min/mg protein) (% reaction) | | |
|---|---|---|
| without inhibitor | with inhibitor | concentration of inhibitor |
| 100 ± 9.1 | 94.4 ± 1.2 | 1 mg/l |
| 100 ± 8.1 | 53.8 ± 3.8 | 10 mg/l |
| 100 ± 5.5 | 16.2 ± 3.2 | 100 mg/l | inhibitor = 9-hydroxy-10(trans)-12(cis)-octadecadienic acid.

The values obtained show a clear inhibition of aromatase by the inventively used fatt acid.

EXAMPLE 4

Inhibition of Aromatase Activity with 9-hydroxy-10(trans)-12(cis)-octadecadienic acid.

Further inhibition tests were carried out in the manner as described for Example 3, with 9-hydroxy-10(trans)-12(cis)-octadecadienic acid and with trihydroxy-10(trans)-12(cis)-octadecadienic acid as the inhibitors. The solvent for the fatty acids was also examined for counter-control. The conditions of the inhibition tests are shown in table 3. The resulting aromatase activity is shown as percent of reaction in table 4. The values obtained for absolute aromatase activity are average values from three measurements in each case, and additionally the standard deviation is given; the test without inhibitor is an average value out of nine measured values.

TABLE 3

| Experimental conditions of aromatase inhibition | |
|---|---|
| Volume of test batch: | 500 ul |
| enzyme source: | placenta microsomes 40 ug protein |
| substrate: | androstenedione (100 nM) |
| tracer: | $^3$H-androstenedione |
| co-substrate: | NADPH-regenerating system (0.5 mM) |
| incubation time: | 10 minutes |
| measured product: | $^3H_2O$ |
| detection: | LSC |

TABLE 4

| | Aromatase activity (pMol/10 min/mg protein) (% reaction) | | |
|---|---|---|---|
| | concentration of the inhibitor | | |
| | 1 mg/l | 10 mg/l | 100 mg/l |
| without inhibitor | 100 ± 9.1 | 100 ± 8.1 | 100 ± 5.5 |
| with inhibitor | | | |
| 9-oxo-10(trans)-12(cis)-octadecadienic acid | 58.3 ± 3.6 | 19.3 ± 3.4 | 6.2 ± 2.9 |
| trihydroxy-10(trans)-12(cis)-octadecadienic acid | 54.1 ± 7.6 | 31/3 ± 2.0 | 27.1 ± 5.4 |
| solvent (counter-control) | 95.9 ± 8.6 | 89.6 ± 9.4 | 102.1 ± 7.2 | average value ± S.D. (n = 3)

The values obtained demonstrate a clear inhibition of aromatase by the inventive fatty acids.

From tables 2 and 4 the inhibition of aromatase activity by the fatty acids employed is discernible. It is shown especially that the keto form of the octadecadienic acid has a stronger aromatase inhibiting effect. This effect is about 10 times stronger than in the acid in hydroxy form, which shows in a displacement with respect to the concentration of the inhibitor. The trihydroxy-10(trans)-12(cis)-octadedecadienic acid also shows an inhibiting effect, whose order of magnitude corresponds to the effect of the above-named oxo acid.

While the preferred compositions and methods are illustrated in the foregoing description, many variations in materials and in the details of the illustrated method and compositions will occur to those skilled in the art. It is intended that all such variations which fall within the scope and spirit of the appended claims be embraced thereby.

I claim:

1. A method for treating a mammal suffering from disease induced by estrogen, which method comprises: administering to a subject in need of such treatment a pharmaceutical composition containing a therapeutically effective amount of a compound selected from hydroxyoctadecadienic acid, the keto form, or an ester derivative thereof.

2. The method of claim 1, wherein the ester derivative is a low alkyl ester having 1 to 4 carbon atoms.

3. The method of claim 1, wherein the disease induced by estrogen is an estrogen-dependent cancer.

4. The method of claim 1, wherein the disease induced by estrogen is breast carcinoma.

5. The method of claim 1, wherein the disease induced by estrogen is benign prostatic hyperplasia.

6. The method of claim 1, wherein the hydroxyoctadecadienic acid contains at least one hydroxy group on the carbon at position 9, 10, 11, 12, or 13.

7. The method of claim 1, wherein the keto form of hydroxyoctadecadienic acid contains at least one oxo group on the carbon at position 9, 10, 11, 12, or 13.

8. The method of claim 6, wherein the hydroxyoctadecadienic acid is 9-hydroxy-10(trans)-12(cis)-octadecadienic acid.

9. The method of claim 6, wherein the hydroxyoctadecadienic acid is 13-hydroxy-9(cis)-11(trans)-octadecadienic acid.

10. The method of claim 7, wherein the keto form of the hydroxyoctadecadienic acid is 9-oxo-10(trans)-12(cis)-octadecadienic acid.

11. The method of claim 7, wherein the keto form of the hydroxyoctadecadienic acid is 13-oxo-9(cis)-11(trans)-octadecadienic acid.

12. The method of claim 1, wherein up to three hydroxy groups are present in the hydroxyoctadecadienic acid.

13. The method of claim 12, wherein the hydroxyoctadecadienic acid is trihydroxyoctadecadienic acid.

14. The method of claim 1, wherein up to three oxo groups are present in the keto form of the hydroxyoctadecadienic acid.

15. The method of claim 1, wherein said pharmaceutical composition is administered orally or by injection.

16. The method of claim 15, wherein said oral administration is by tablet, capsule, or dragee.

17. The method of claim 15, wherein said injection is intramuscular injection.

18. The method of claim 14, wherein said injection isparenternal injection of the pharmaceutical composition in alcohol solution.

19. The method of claim 1, wherein said therapeutically effective amount is from about 50 to about 200 mg of the hydroxyoctadecadienic acid or keto form thereof, or a corresponding amount of the ester derivative thereof.

* * * * *